(12) United States Patent
Hertel et al.

(10) Patent No.: US 7,294,638 B2
(45) Date of Patent: Nov. 13, 2007

(54) TREATMENT OF ADHD

(75) Inventors: Klaus Peter Hertel, Charlottenlund (DK); Jorn Arnt, Solrod Strand (DK)

(73) Assignee: H. Lundbeck A/S, Copenhagen (DK)

( * ) Notice: Subject to any disclaimer, the term of this patent is extended or adjusted under 35 U.S.C. 154(b) by 622 days.

(21) Appl. No.: 10/477,382

(22) PCT Filed: May 7, 2002

(86) PCT No.: PCT/DK02/00298

§ 371 (c)(1),
(2), (4) Date: Nov. 7, 2003

(87) PCT Pub. No.: WO02/089797

PCT Pub. Date: Nov. 14, 2002

(65) Prior Publication Data

US 2004/0152737 A1 Aug. 5, 2004

(30) Foreign Application Priority Data

May 9, 2001 (DK) .............................. 2001 00732

(51) Int. Cl.
*A61K 31/445* (2006.01)
(52) U.S. Cl. .................... 514/339; 546/277.4
(58) Field of Classification Search ............. 546/277.4; 514/339
See application file for complete search history.

(56) References Cited

U.S. PATENT DOCUMENTS 5,521,197 A 5/1996 Audia
6,262,087 B1 * 7/2001 Perregaard et al. ......... 514/339
6,656,953 B2 * 12/2003 Hoemann ................... 514/317

FOREIGN PATENT DOCUMENTS

WO WO-98/28293 A1 7/1998

OTHER PUBLICATIONS

Tarazi et al. I, "Dopamine D4 receptos, etc.," Molecular Psychiatry, 1999, 4, 529-538.*
Paterson et al., "Dopamine D4 Receptor, etc.," Neuropsychopharmacology, 1999, 21 (1) 3-16.*
Todd et al., "The dopamine receptor, etc.," Trends in Pharmacological Sciences 22 (2), 2001, 55-56.*
Tarazi et al., II, "Dopamine D4 Receptors, etc.," Journal of Receptors and Signal Transduction, 24 (3), 2004, 131-147.*
J.T. McCracken, et al., "Evidence for linkage of a tandem duplication polymorphism upstream of the dopamine D4 receptor gene (DRD4) with attention deficit hyperactivity disorder (ADHD)", Molecular Psychiatry, vol. 5, (2000), pp. 531-536.

* cited by examiner

*Primary Examiner*—Patricia L. Morris
(74) *Attorney, Agent, or Firm*—Darby & Darby

(57) ABSTRACT

The use of 3-[1-[2-(1-acetyl-2,3-dihydro-1H-indol-3-yl) ethyl]-1,2,3,6-tetrahydropyridin-4-yl]-6-chloro-1H-indole, any of its enantiomers and pharmaceutically acceptable salts thereof for the preparation of a pharmaceutical composition for the treatment of attention deficit hyperactivity disorder.

3 Claims, No Drawings

TREATMENT OF ADHD

The present invention relates to the use of 3-[1-[2-(1-acetyl-2,3-dihydro-1H-indol-3-yl)ethyl]-1,2,3,6-tetrahydropyridin-4-yl]-6-chloro-1H-indole, its enantiomers and pharmaceutically acceptable salts thereof for the preparation of medicaments useful for the treatment of ADHD (attention deficit hyperactivity disorder).

BACKGROUND OF THE INVENTION

ADHD refers clinically to a relatively common syndrome (epidemiologic studies have suggested that the prevalence of ADHD among the general population is between 2-10%). ADHD begins in childhood and typically remits by adulthood (Szatmari *Child Adolesc. Psychiat. Clin. North Am.* 1982, 1, 361-371). ADHD is clinically characterised by inattention (e.g. failure to give close attention, difficulties in sustaining attention, difficulties in organising tasks and activities and easily distracted by extraneous stimuli), hyperactivity (e.g. difficulties in remaining seated, excessive motor activity in inappropriate situations, the patient acts as if "driven by a motor") and impulsivity (e.g. difficulties in awaiting turn, answer questions before they have been completed and often interrupts or intrudes ongoing conversation; American Psychiatric Association, *Diagnostic and Statistical Manual of Mental Disorders (DSM-IV)*, 1994).

Twin studies of ADHD have indicated that around 80% of the etiology of ADHD is attributed to genetic factors (Gjone et al. *J. Am. Acad. Child Adolesc. Psychiat.* 1996, 35, 588-596). Although, the strong genetic component of the disease, the patophysiology of ADHD, is currently not known. Cognitive, physiological and imaging studies indicate that ADHD might involve a dysfunction of the cortical inhibition of subcortical structures (Faraone and Biederman *Neurobiology of Mental Illness*, eds: Charney, Nestler and Bunney, Oxford University Press, 1999, 60, 788-801). Both the tentative involvement of cortical areas and the well-recognised effects of stimulant medication on monoamine metabolism suggest that ADHD might be associated with malfunctioning of the monoaminergic pathways projecting to the cortex (including the dopaminergic and the serotonergic systems).

A very useful animal model of ADHD is the DAT knockout (KO) mice (Gainetdinov et al. *Science* 1999, 283, 397-401). These mice lack the gene encoding the dopamine transporter (DAT) and exhibit pronounced hyperactivity, which can be reversed by psychostimulants such as methylphenidate and amphetamine, drugs frequently used in the pharmacotherapy of ADHD. Interestingly, compounds that increase serotonergic neurotransmission such as the selective serotonin re-uptake inhibitor fluoxetine, the serotonin receptor agonist quipazine as well as the serotonin precursors 5-hydroxytryptophan and L-tryptophan were also found to counteract the hyperactivity in these DAT-KO mice (Gainetdinov et al. *Science* 1999, 283, 397-401).

Several clinical studies have found that tricyclic antidepressant drugs, which block the serotonin transporter, are effective in the treatment of ADHD (Spencer et al. *J. Am. Acad. Child Adolesc. Psychiat.* 1996, 35, 409432; Wilens et al. *J. Clin. Psychopharmacol.* 1995, 15, 270-279). Furthermore, there is also evidence that the selective serotonin re-uptake inhibitor fluoxetine is effective in reducing symptoms of ADHD (Barrickman et al. *J. Am. Acad. Child Adolesc. Psychiat.* 1991, 30, 762-767).

However, psychostimulants, particularly methylphenidate and dextroamphetamine, have been and continue to be the drugs of choice in treating patients with ADHD (Faraone and Biederman, In: *Neurobiology of Mental Illness*, eds: Charney, Nestler and Bunney, Oxford University Press, 1999, 60, 788-801). Although psychostimulants appear effective, there are a number of problems associated with their use in the treatment of ADHD patients. For example, some patients do not respond at all or only partially to treatment. Furthermore, adverse effects such as insomnia, decreased appetite, irritability, tics and depressive symptoms after long-term treatment are relatively frequent in ADHD patients treated with psychostimulants.

Consequently, there is still a large unmet need for efficient and better tolerated drugs for the treatment of this condition.

WO 98/28293 describes a series of substituted indane and dihydroindole compounds having effect at dopamine $D_4$ receptors. The compounds described are considered useful for the treatment of a range of psychiatric and neurological disorders, including the positive and negative symptoms of schizophrenia, other psychoses, anxiety disorder, such as generalised anxiety disorder, panic disorder and obsessive compulsive disorder, depression, alcohol abuse, impulse control disorders, aggression, side effects induced by conventional antipsychotic agents, ischaemic disease states, migraine, senile dementia, cardiovascular disorders and for the improvement of sleep.

It has now, surprisingly, been found that a compound of WO 98/28293, namely 3-[1-[2-(1-acetyl-2,3-dihydro-1H-indol-3-yl)ethyl]-1,2,3,6-tetrahydropyridin-4-yl]-6-chloro-1H-indole having the formula

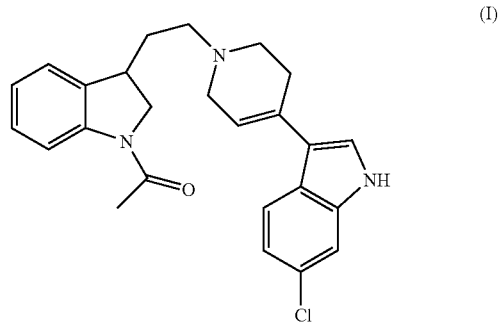

(I)

which is described herein as a potent dopamine $D_4$ ligand, may be particularly useful in the treatment of attention deficit hyperactivity disorder.

SUMMARY OF THE INVENTION

Thus, the present invention relates to the use of 3-[1-[2-(1-acetyl-2,3-dihydro-1H-indol-3-yl)ethyl]-1,2,3,6-tetrahydropyridin-4-yl]-6-chloro-1H-indole having the formula (I), any of its enantiomers and pharmaceutically acceptable salts thereof for the treatment of attention deficit hyperactivity disorder.

In particular, the invention relates to the use of (S)-(+)-3-[1-[2-(1-acetyl-2,3-dihydro-1H-indol-3-yl)ethyl]-1,2,3,6-tetrahydropyridin-4-yl]-6-chloro-1H-indole and pharmaceutically acceptable salts thereof for the treatment of attention deficit hyperactivity disorder.

The present invention also relates to the use of 3-[1-[2-(1-acetyl-2,3-dihydro-1H-indol-3-yl)ethyl]-1,2,3,6-tetrahydropyridin-4-yl]-6-chloro-1H-indole having formula (I), any of its enantiomers, but in particular (S)-(+)-3-[1-[2-(1-acetyl-2,3-dihydro-1H-indol-3-yl)ethyl]-1,2,3,6-tetrahydropyridin-4-yl]-6-chloro-1H-indole, and pharmaceutically acceptable salts for the preparation of a pharmaceutical composition for the treatment of attention deficit hyperactivity disorder.

DETAILED DESCRIPTION OF THE INVENTION

The compound 3-[1-[2-(1-acetyl-2,3-dihydro-1H-indol-3-yl)ethyl]-1,2,3,6-tetrahydropyridin-4-yl]-6-chloro-1H-indole and its enantiomers were first disclosed in WO 98/28293. This application also contains data showing that the compound is a potent dopamine $D_4$ ligand.

The present invention covers the use of both the racemate of the compound of formula (I) and each of its enantiomers for the treatment of attention deficit hyperactivity disorder.

The compound of formula (I) and its enantiomers and pharmaceutically acceptable salts thereof may be prepared as described in WO 98/28293, see in particular example 20 and 34.

The compound, (S)-(+)-3-[1-[2-(1-acetyl-2,3-dihydro-1H-indol-3-yl)ethyl]-1,2,3,6-tetrahydropyridin-4-yl]-6-chloro-1H-indole, has been tested in the DAT-KO mice, an animal model which have many behaviour patterns and responses to psychostimulants in common with individuals with ADHD (Gainetdinov et al. *Science* 1999, 283, 397-401). The compound was found to have effect in this model.

Pharmaceutical Compositions

The pharmaceutical compositions according to the invention may be prepared by conventional methods in the art.

Thus, tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilising the solution and filling it in suitable ampules or vials. Any suitable additive conventionally used in the art may be added, such as tonicity agents, preservatives, antioxidants, etc.

The invention claimed is:

1. A method for the treatment of attention deficit hyperactivity disorder comprising administering an effective amount of a compound 3-[1-[2-(1-acetyl-2,3-dihydro-1H-indol-3-yl)ethyl]-1,2,3,6-tetrahydropyridin-4-yl]-6-chloro-1H-indole having the formula

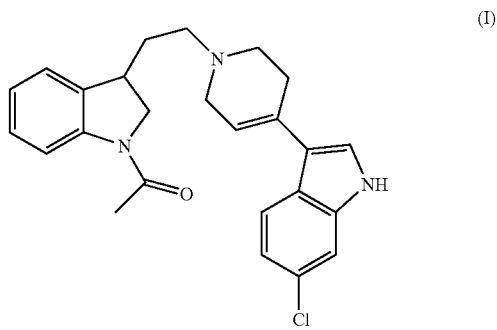

(I)

an enantiomer of said compound, or a pharmaceutically acceptable salt of said compound or enantiomer to an individual in need thereof.

2. The method according to claim 1 wherein the compound used is (S)-(+)-3-[1-[2-(1-acetyl-2,3-dihydro-1H-indol-3-yl)ethyl]-1,2,3,6-tetrahydropyridin-4-yl]-6-chloro-1H-indole or a pharmaceutically acceptable salt thereof.

3. The method according to claim 1 wherein the compound used is (R)-(−)-3-[1-[2-(1-acetyl-2,3-dihydro-1H-indol-3-yl)ethyl]-1,2,3,6-tetrahydropyridin-4-yl]-6-chloro-1H-indole or a pharmaceutically acceptable salt thereof.

* * * * *